United States Patent [19]
Wu

[11] Patent Number: 4,553,273
[45] Date of Patent: Nov. 19, 1985

[54] VERTEBRAL BODY PROSTHESIS AND SPINE STABILIZING METHOD

[75] Inventor: Kent K. Wu, Royal Oak, Mich.

[73] Assignee: Henry Ford Hospital, Detroit, Mich.

[21] Appl. No.: 555,362

[22] Filed: Nov. 23, 1983

[51] Int. Cl.[4] .......................... A61F 1/24; A61F 1/00; A61F 5/04
[52] U.S. Cl. .................................... 623/18; 128/92 B; 128/92 C; 128/92 E
[58] Field of Search ................ 3/1.9, 1.91; 128/92 R, 128/92 B, 92 BC, 92 C, 92 D, 92 E, 69

[56] References Cited

U.S. PATENT DOCUMENTS

| | | | |
|---|---|---|---|
| 4,156,296 | 5/1979 | Johnson et al. | 3/1.91 |
| 4,289,123 | 9/1981 | Dunn | 128/92 B X |
| 4,401,112 | 8/1983 | Rezaian | 3/1.91 X |

FOREIGN PATENT DOCUMENTS

| | | | |
|---|---|---|---|
| 3023353 | 4/1981 | Fed. Rep. of Germany | 3/1.91 |
| 2194123 | 2/1974 | France | 3/1.9 |

OTHER PUBLICATIONS

The Marmour Tibial Plateau Prosthesis (Advertisement by Richards Mfg. Company), The Journal of Bone & Joint Surgery, vol. 52-A, No. 8, Dec. 1970.

Primary Examiner—Ronald L. Frinks
Attorney, Agent, or Firm—Barnes, Kisselle, Raisch, Choate, Whittemore & Hulbert

[57] ABSTRACT

A method and apparatus for stabilizing the spine wherein vertebral bodies have been removed which comprises forming recesses in the vertebral bodies which face one another, inserting a longitudinally extendable prosthetic device between the opposed vertebral bodies with the ends of the prosthetic device engaging the recesses, extending the prosthetic device to the desired predetermined distance.

8 Claims, 7 Drawing Figures

U.S. Patent   Nov. 19, 1985   4,553,273
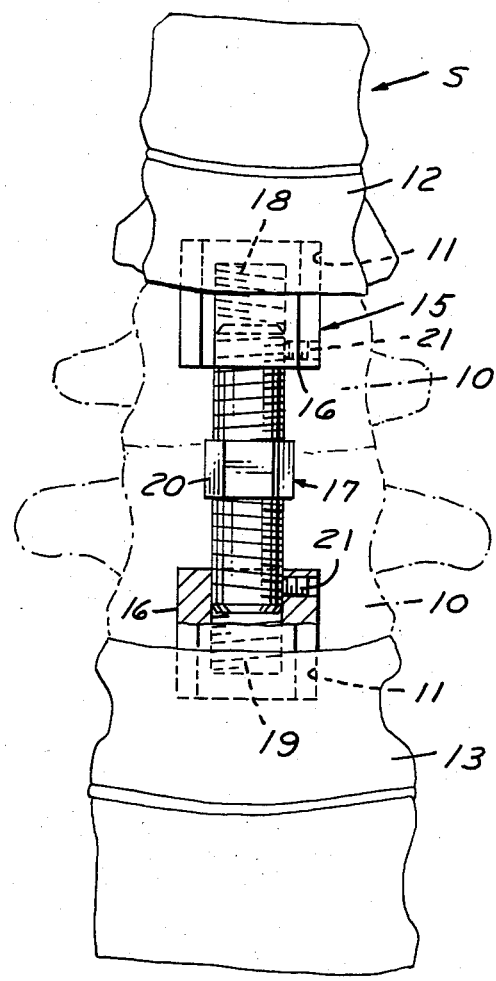
FIG.1
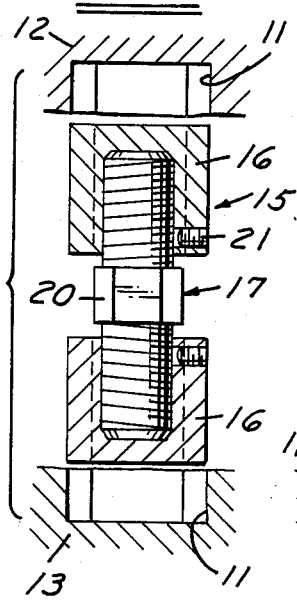
FIG.5
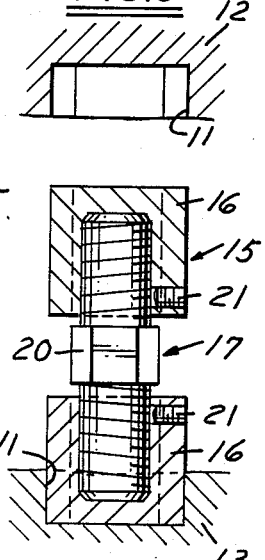
FIG.6
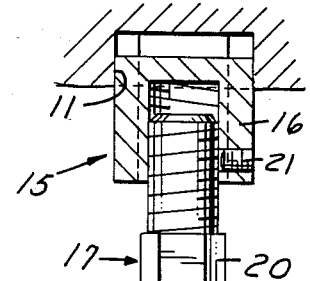
FIG.7
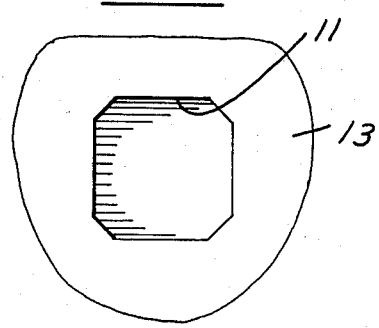
FIG.2
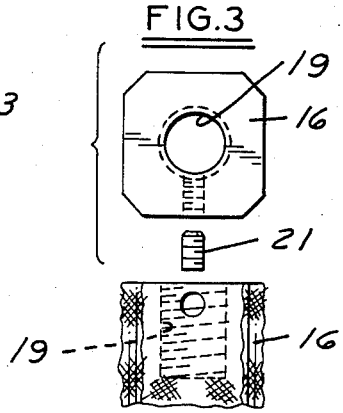
FIG.3
FIG.4

VERTEBRAL BODY PROSTHESIS AND SPINE STABILIZING METHOD

This invention relates to the stabilization of the spine where portions of the spine are removed because of disease or injury.

BACKGROUND AND SUMMARY OF THE INVENTION

Where portions of the spine need to be removed because of disease or injury, it has been common to utilize a bone graft, known as bone fusion, to span the gap between the portions of the spine that remain after the removal of other portions. Bone fusion requires a long period of recovery and rehabilitation. Where the portions of the spine that are removed comprise vertebral bodies, the bone fusion sometimes is unable to withstand the heavy load of the body and therefore restricts the movement of the patient.

Among the objects of the present invention are to provide a method and apparatus for stabilizing the spine wherein vertebral bodies have been removed; which method and apparatus effectively supports the weight of the spine; and which method and apparatus permits the patient to move readily shortly after the removal of the vertebral bodies.

In accordance with the invention, the method and apparatus for stabilizing the spine wherein vertebral bodies hae been removed which comprises forming recesses in the vertebral bodies which face one another, inserting a longitudinally extendable prosthetic device between the opposed vertebral bodies with the ends of the prosthetic device engaging the recesses, and extending the prosthetic device to the desired predetermined distance.

DESCRIPTION OF THE DRAWINGS

FIG. 1 is a front elevational view of a portion of a spine having the prosthesis positioned therein.

FIG. 2 is a fragmentary plan view of a portion of a vertebral body for receiving the prosthetic device.

FIG. 3 is a plan view of a portion of the prosthetic device.

FIG. 4 is an elevational view of a portion of the prosthesis.

FIGS. 5-7 are elevational views showing various steps in the insertion of the prosthetic device.

DESCRIPTION

Referring to FIG. 1, there is shown a spine S wherein vertebral bodies 10 have been removed leaving a gap or space.

In accordance with the invention, the surgeon forms recesses 11 in the bodies 12, 13 (FIG. 2) adjacent to the bodies 10 which have been removed, such that the recesses face one another. A prosthetic device 15 comprising spaced non-circular blocks 16 is positioned in the recesses 11. The recesses 11 are non-circular and preferably polygonal as are the cross sections of the blocks 16. The blocks 16 are bounded by continuously flat bases and are interconnected by a shaft 17 that has threads on the ends engaging complementary threads in the blocks 16. Threads on the opposite ends of the shaft 17 are opposite and the threads 18 on one block 16 are opposite the threads 19 on the other block 16 so that rotation of the shaft 17 will extend or retract the blocks 16. The central portion 20 of each shaft is non-circular and preferably polygonal so that it can readily be grasped to extend or retract the blocks 16. As shown in FIGS. 3 and 4 the block 16 is generally square in cross-section and has bevelled axial surfaces at the juncture of the sides.

After the recesses 11 are formed, the prosthetic device 15 is brought into position (FIG. 5), one block is engaged with a recess 11 (FIG. 6) and the shaft 17 is rotated to extend the blocks so that they engage the recesses (FIG. 7) and the rotation is continued until the space between opposed vertebral bodies 12, 13 is bridged and the desired distance is provided between the opposed vertebral bodies 12, 13 (FIG. 1). A set screw 21 is then rotated to lock each body in the desired position.

The phosthetic device 15 comprising the blocks 16, threaded shaft 17 and set screws 21 is preferably made of stainless steel and the external surface of the blocks 16 which engage the recesses 11 that are formed in the vertebral bodies is preferably roughened or sintered (as shown in FIG. 4) so that when bone growth occurs in the vertebral bodies, a more effective interlock will occur between the vertebral body portions and the blocks of the prosthesis.

Alternatively, bone cement can be utilized in the recesses 11 to assist in holding the blocks 16 in position.

It can thus be seen that there has been provided a method and apparatus which effectively stabilizes the spine where vertical bodies have been removed; which can be applied promptly after the removal of vertebral bodies and which will effectively permit the patient to move promptly after the operation.

In accordance with the invention, the prosthetic devices can be provided in various lengths and cross sections depending on the area to be bridged and the size of the patient.

I claim:

1. The method for stabilizing the spine wherein vertebral bodies have been removed which comprises forming non-circular recesses in the vertebral bodies which face one another and which have flat bases, inserting a longitudinally extendable prosthetic device having spaced non-circular blocks having non-circular cross-section conforming to the configurations of the non-circular recesses and flat bases abutting said flat bases of said recesses and extendable means between said blocks between the opposed vertebral bodies with the blocks of the prosthetic device in position for engagement with said recesses, extending the prosthetic device to the desired predetermined distance to engage each block in its respective recess and locking the prosthetic device in extended position.

2. A prosthetic device for stabilizing the spine wherein vertebral bodies have been removed which comprises a pair of non-circular blocks which are bounded by continuously flat bases for engaging non-circular recesses having flat bases in the remaining vertebral bodies which face one another, and extendable means between said blocks for moving said blocks into engagement with the recesses in the vertebral bodies.

3. The prosthetic device set forth in claim 2 including means between the blocks and the extensible means for locking said blocks in extended position.

4. The prosthetic device set forth in claim 2 wherein said blocks have a non-circular cross section.

5. The prosthetic device set forth in claim 2 wherein said blocks having roughened surfaces whereby bone growth will provide a bond with said blocks.

6. The prosthetic device set forth in claim 2 wherein said extendible means comprises a single shaft, said shaft having threads on the ends thereof which are opposite, said blocks having complimentary opposite threads.

7. The prosthetic device set forth in claim 6 wherein said prosthetic device includes set screw means associated with each said block and engaging the shaft.

8. The prosthetic device set forth in claim 2 wherein said block is generally square in cross-section and has beveled axial surfaces at the juncture of the sides thereof.

* * * * *